US 11,918,759 B2

(12) United States Patent
Tanaka et al.

(10) Patent No.: US 11,918,759 B2
(45) Date of Patent: Mar. 5, 2024

(54) MEDICAL BRAIDED TUBE ASSEMBLY

(71) Applicant: Hitachi Metals, Ltd., Tokyo (JP)

(72) Inventors: Kotaro Tanaka, Tokyo (JP); Takanobu Watanabe, Tokyo (JP); Kimika Kudo, Tokyo (JP); Takanori Komuro, Tokyo (JP)

(73) Assignee: PROTERIAL, LTD., Tokyo (JP)

( * ) Notice: Subject to any disclaimer, the term of this patent is extended or adjusted under 35 U.S.C. 154(b) by 352 days.

(21) Appl. No.: 17/035,182

(22) Filed: Sep. 28, 2020

(65) Prior Publication Data

US 2021/0093831 A1    Apr. 1, 2021

(30) Foreign Application Priority Data

Sep. 30, 2019  (JP) .................................. 2019-179828

(51) Int. Cl.
| | | |
|---|---|---|
| *A61M 25/00* | (2006.01) | |
| *A61M 39/10* | (2006.01) | |
| *A61M 5/00* | (2006.01) | |
| *A61M 25/10* | (2013.01) | |

(52) U.S. Cl.
CPC .......... *A61M 25/005* (2013.01); *A61M 39/10* (2013.01); *A61M 5/007* (2013.01); *A61M 25/104* (2013.01); *A61M 2205/3331* (2013.01)

(58) Field of Classification Search
CPC .......... A61M 25/0012; A61M 25/0014; A61M 25/005; A61M 25/0052; A61M 25/0053; A61M 25/0097; A61M 2025/0059; A61M 39/08
See application file for complete search history.

(56) References Cited

U.S. PATENT DOCUMENTS

| | | |
|---|---|---|
| 3,540,486 A | 11/1970 | Flounders |
| 3,722,550 A | 3/1973 | Matthews |
| 4,068,659 A * | 1/1978 | Moorehead ......... A61M 25/065 604/523 |
| 4,330,017 A | 5/1982 | Satoh et al. |

(Continued)

FOREIGN PATENT DOCUMENTS

| | | |
|---|---|---|
| JP | 2008-086340 A | 4/2008 |
| JP | 2015-019851 A | 2/2015 |

(Continued)

OTHER PUBLICATIONS

Office Action issued in corresponding Japanese Patent Application No. 2019-179828 dated Oct. 4, 2022; 7 pages.

*Primary Examiner* — Kami A Bosworth (74) *Attorney, Agent, or Firm* — Thomas W. Cole; Calderon Safran & Cole P.C.

(57) ABSTRACT

A medical braided tube assembly includes a braided tube including a hollow cylindrical inner resin layer, a braided wire including braided strands and being provided over a periphery of the inner resin layer, and an outer resin layer provided to cover peripheries of the inner resin layer and the braided wire, and a connector provided at an end portion of the braided tube. The connector includes a tube housing section for accommodating the end portion of the braided tube. The braided tube accommodated in the tube housing section are adhesively fixed by an adhesive. The adhesive is provided to seal an entire periphery of the braided wire at an end face of the braided tube.

13 Claims, 4 Drawing Sheets

(56) References Cited

U.S. PATENT DOCUMENTS

| | | | | |
|---|---|---|---|---|
| 4,695,276 | A | * | 9/1987 | Shinno .............. A61M 25/0014 604/905 |
| 5,613,523 | A | | 3/1997 | Klawuhn et al. |
| 5,622,210 | A | | 4/1997 | Crisman et al. |
| 5,690,146 | A | | 11/1997 | Stammen |
| 5,730,733 | A | * | 3/1998 | Mortier ............... A61M 25/005 604/527 |
| 5,797,886 | A | * | 8/1998 | Roth ................... A61J 15/0092 604/264 |
| 6,179,008 | B1 | | 1/2001 | Kawazura et al. |
| D499,465 | S | | 12/2004 | Paul, III |
| 6,841,214 | B1 | * | 1/2005 | Keith ....................... D04C 3/34 428/35.8 |
| 9,857,001 | B2 | | 1/2018 | Manas-Zloczower |
| 10,458,573 | B2 | | 10/2019 | Burrowes |
| 10,779,741 | B2 | | 9/2020 | Nemec et al. |
| 10,952,629 | B2 | | 3/2021 | Nemec et al. |
| 2004/0134555 | A1 | | 7/2004 | Powell et al. |
| 2005/0199308 | A1 | | 9/2005 | Swails et al. |
| 2006/0264904 | A1 | * | 11/2006 | Kerby ............... A61M 25/0021 604/523 |
| 2014/0326355 | A1 | | 11/2014 | Nonaka et al. |
| 2017/0202468 | A1 | | 7/2017 | Nemec et al. |
| 2020/0268268 | A1 | | 8/2020 | Nemec et al. |

FOREIGN PATENT DOCUMENTS

| | | |
|---|---|---|
| JP | 2017-018278 A | 1/2017 |
| JP | 2019-503216 A | 2/2019 |

\* cited by examiner

MEDICAL BRAIDED TUBE ASSEMBLY

CROSS-REFERENCE TO RELATED APPLICATION

The present application is based on Japanese Patent Application No. 2019-179828 filed on Sep. 30, 2019, the entire contents of which are incorporated herein by reference.

BACKGROUND OF THE INVENTION

1. Field of the Invention

The present invention relates to a medical braided tube assembly.

2. Description of the Related Art

For example, in percutaneous coronary angioplasty (PTCA) and percutaneous angioplasty (PTA), a braided tube has been used as a pressure resistant tube used for an indeflator for inflating and deflating a dilatation balloon catheter, or the like. At an end of the braided tube, a connector is provided for connection with the dilatation balloon catheter or the like. Hereinafter, a braided tube provided with a connector at its end is referred to as a medical braided tube assembly.

As prior art document information related to the invention of this application, there is JP2015-19851A.

[Patent Document 1] JP2015-19851A

SUMMARY OF THE INVENTION

In the above-mentioned indeflator, a high pressure is applied to a working fluid flowing through the medical braided tube assembly in order to inflate the dilatation balloon catheter against the blood pressure. Therefore, the medical braided tube assembly is required to have high pressure resistance.

Therefore, it is an object of the present invention to provide a medical braided tube assembly with improved pressure resistance.

For the purpose of solving the above-described problems, the present invention provides a medical braided tube assembly comprising:

a braided tube comprising a hollow cylindrical inner resin layer, a braided wire including braided strands and being provided over a periphery of the inner resin layer, and an outer resin layer provided to cover peripheries of the inner resin layer and the braided wire; and a connector provided at an end portion of the braided tube, wherein the connector includes a tube housing section for accommodating the end portion of the braided tube, wherein the braided tube accommodated in the tube housing section is adhesively fixed by an adhesive, wherein the adhesive is provided to seal an entire periphery of the braided wire at an end face of the braided tube.

POINTS OF THE INVENTION

According to the present invention, it is possible to provide a medical braided tube assembly with improved pressure resistance.

DETAILED DESCRIPTION OF THE PREFERRED EMBODIMENT

Embodiment

Hereinafter, an embodiment of the present invention will be described with reference to the appended drawings.

(Explanation of an Indeflator Using a Braided Tube)

Figure 1:
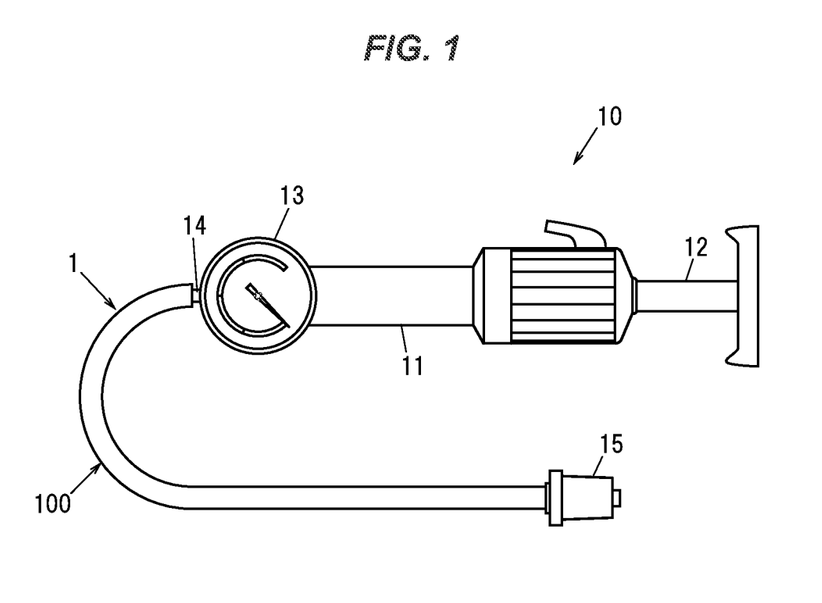
FIG. 1 is a plan view of an indeflator using a medical braided tube assembly according to an embodiment of the present invention.

FIG. 1 is a plan view of an indeflator 10 using a medical braided tube assembly 100 according to an embodiment of the present invention. The indeflator 10 is configured for inflating and deflating a dilatation balloon catheter in percutaneous coronary angioplasty (PTCA) or percutaneous angioplasty (PTA).

As shown in FIG. 1, the indeflator 10 is a so-called plunger pump (or piston pump) that delivers or sucks a working fluid such as a contrast agent, and includes a cylinder 11, a plunger (or piston) 12, and a pressure gauge 13 for detecting the pressure of the working fluid inside the cylinder 11.

In the indeflator 10, one end of the braided tube 1 is connected to a liquid inlet/outlet 14 for discharging or sucking the working fluid. The other end of the braided tube 1 is provided with a connector (luer connector) 15. In the present embodiment, a dilatation balloon catheter (not shown) is connected to the connector 15. The medical braided tube assembly 100 according to the present embodiment is constituted by the braided tube 1 and the connector 15 at the end of the braided tube 1.

In the indeflator 10, the plunger 12 is moved back and forth to pressurize and depressurize the working fluid to inflate and deflate (expand and contract) the dilatation balloon catheter. At this time, for example, if air bubbles are mixed in the medical braided tube assembly 100, the working fluid may not be pressurized or depressurized as intended, and the dilatation balloon catheter may perform an unintended operation. In addition, since a transparent liquid may be used as the working fluid, the medical braided tube assembly 100 is required to have high transparency in such a manner that the transparent liquid flowing through the inside of the medical braided tube assembly 100 and the outer shape of the bubbles contained in the liquid can be visually observed. Further, when the working fluid is pressurized, if a part of the braided tube 1 is expanded, or leakage or the like occurs at the connecting portion between the connector 15 and the braided tube 1, the working fluid will not be pressurized as intended and the dilatation balloon catheter may perform an unintended operation. Therefore, the medical braided tube assembly 100 is required to have high pressure resistance.

(Explanation of the Braided Tube 1)

Figure 2A:
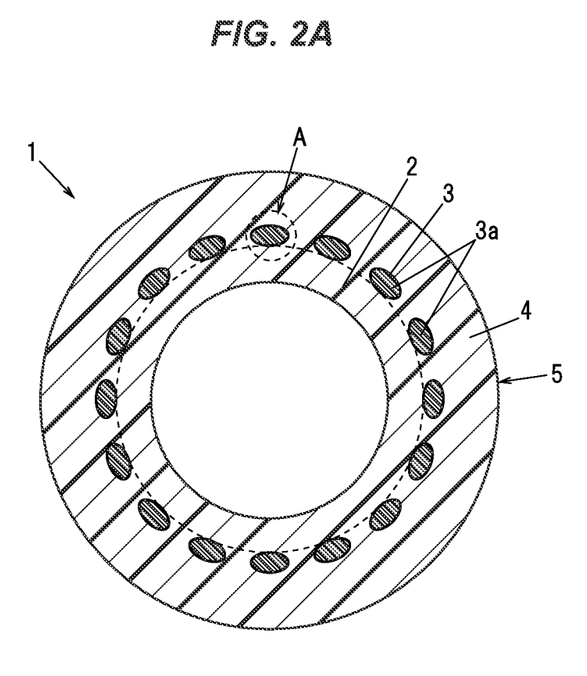
FIG. 2A is a cross-sectional view showing a cross section of a braided tube in a direction perpendicular to a tube longitudinal direction.
Figure 2B:
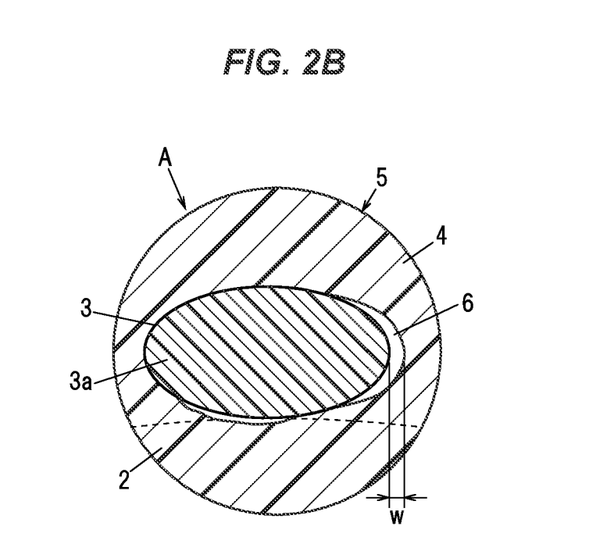
FIG. 2B is an enlarged view of a part A of the braided tube in FIG. 2A.

First, details of the braided tube 1 in the medical braided tube assembly 100 will be described. FIG. 2A is a cross-sectional view showing a cross section of the braided tube 1 in a direction perpendicular to a tube longitudinal direction. FIG. 2B is an enlarged view of a part A of the braided tube 1 in FIG. 2A.

As shown in FIGS. 2A and 2B, the braided tube 1 includes a hollow cylindrical inner resin layer and 2, a braided wire 3 formed by braiding strands (elemental wires) 3a over a periphery of the inner resin layer 2, and an outer resin layer 4 provided so as to cover peripheries of the inner resin layer 2 and the braided wire 3.

The inner resin layer 2 and the outer resin layer 4 are made of a material that transmits visible light. In the present embodiment, the inner resin layer 2 and the outer resin layer 4 are made of thermoplastic polyurethane resin (TPU). Hereinafter, the inner resin layer 2 and the outer resin layer 4 are collectively referred to as a resin layer 5. In the present embodiment, an inner diameter of the resin layer 5 (an inner diameter of the inner resin layer 2) is 1.70 mm or more and 1.90 mm or less, and an outer diameter of the resin layer 5 (an outer diameter of the outer resin layer 4) is 3.50 mm or more and 3.70 mm or less. An entire thickness of the resin layer 5 is 0.80 mm or more and 1.00 mm or less.

The outer resin layer 4 is configured to enter into gaps between the strands 3a of the braided wire 3 in such a manner that the outer resin layer 4 is in contact with the peripheries of the strands 3a without any gap as close as possible (it will be described later in more detail). Further, the outer resin layer 4 and the inner resin layer 2 are fused and integrated by heat generated when the outer resin layer 4 is molded. A melting point of a resin constituting the outer resin layer 4 is preferably higher than a melting point of a resin constituting the inner resin layer 2 such that the outer resin layer 4 and the inner resin layer 2 are fused and integrated by the heat generated when the outer resin layer 4 is molded.

The strand 3a of the braided wire 3 is made of nylon. Further, as the strand 3a of the braided wire 3, it is preferable to use a non-colored material in order to increase the transparency of the braided tube 1. Non-colored nylon is a transparent material that transmits visible light. In FIGS. 2A and 2B, a cross-sectional shape of the strands 3a is elliptical, but this is because that the strands 3a are arranged along a direction which is inclined with the tube longitudinal direction, and the cross-sectional shape of the strand 3a in the direction perpendicular to the tube longitudinal direction is circular.

An outer diameter of the strand 3a of the braided wire 3 is preferably 0.20 mm or less. This is because if the strand 3a of the braided wire 3 is too thick, it may be difficult to visually recognize the liquid flowing through the braided tube 1 and the bubbles contained in the liquid (that is, the transparency may be reduced). By making the outer diameter of the strand 3a as thin as 0.20 mm or less, the braided wire 3 becomes inconspicuous, and the transparent liquid flowing through the braided tube 1 and the bubbles contained in the liquid are easily visible. In the present embodiment, the strand 3a having an outer diameter of 0.15 mm is used. If the strand 3a is too thin (fine), the pressure resistance may decrease. Therefore, the outer diameter of the strand 3a is preferably 0.10 mm or more.

The present inventors have studied to increase the transparency of the braided tube 1. Then, the present inventors found that, for example, when a strong pulling force is applied to the braided tube 1 along the tube longitudinal direction, the braided wire 3 becomes white in noticeable state, so that it becomes difficult to visually recognize the transparent liquid flowing through the braided tube 1 and the bubbles contained in the liquid. As a result of further study, the present inventors found that the braided wire 3 becomes white and noticeable since the strand 3a of the braided wire 3 is peeled off from the resin layer 5 around the braided wire 3 and a void is formed around the strand 3a.

Therefore, in the braided tube 1 according to the present embodiment, a width w of a void (gap) 6 formed around the strand 3a of the braided wire 3 is 30 μm or less in the cross section perpendicular to the tube longitudinal direction. The width w of the void 6 is the shortest distance between an outer surface of the strand 3a and the resin layer 5 (the inner resin layer 2 or the outer resin layer 4) that face each other across the void 6 in the cross section perpendicular to the tube longitudinal direction. By reducing the width w of the void 6 to 30 μm or less, the braided wire 3 becomes less noticeable and the transparency of the braided tube 1 is improved. As a result, the transparent liquid flowing inside the braided tube 1 and the outer shape of the bubbles contained in the liquid can be easily visually recognized. In addition, in order to further increase the transparency of the braided tube 1, it is more desirable that the width w of the void 6 be 25 μm or less.

Also, for further increasing the transparency of the braided tube 1, it is more desirable to reduce a proportion of voids 6 that are present at the periphery of the strand 3a, and to increase a proportion of close contact between the strand 3a and the resin layer 5 as small as possible. Specifically, it is desirable that a ratio of an outer peripheral length of the strand 3a facing the void 6 to an outer peripheral length of the entire strands 3a is 60% or less in the cross section perpendicular to the tube longitudinal direction. In other words, it is desirable that the ratio of the outer peripheral length of the strand 3a in close contact with the resin layer 5 to the outer peripheral length of the entire strands 3a is 40% or more in the cross section perpendicular to the tube longitudinal direction.

Figure 3:
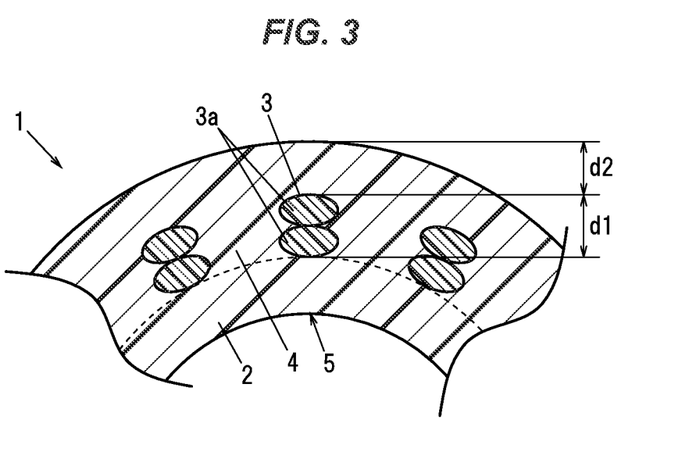
FIG. 3 is an enlarged view of a cross section of the braided tube in FIGS. 2A and 2B at a position where strands of the braided wire are overlapping in a radial direction.

When the outer resin layer 4 is made thinner, irregularities (unevenness) due to the presence/absence of the strand 3a of the braided wire 3 are transferred to the outer surface of the outer resin layer 4, irregularities (unevenness) will occur at the outer surface of the outer resin layer 4 so that the transparency of the braided tube 1 transparency may decrease. Therefore, the thickness of the outer resin layer 4 radially outward of the braided wire 3 is preferably two or more times of the outer diameter of the strand 3a (not less than a thickness d1 of the braided wire 3). More specifically, as shown in FIG. 3, since the braided wire 3 is formed by braiding a plurality of strands 3a, there is one or more positions where the two strands 3a overlap in a tube radial direction. In this position, a thickness d2 of the outer resin layer 4 positioned radially outward the braided wire 3 is not less than the thickness d1 of the braided wire 3. In the present embodiment, the thickness d2 of the outer resin layer 4 positioned radially outward the braided wire 3 is 0.3 mm or more.

Further, in order to increase the pressure resistance of the braided tube 1, it is desired that the inner peripheral surface and the outer peripheral surface of the resin layer 5 have a high degree of concentricity (coaxiality). This is because if the concentricity is low, the resin layer 5 will be partially thin and a thin portion will be deformed (expanded) when pressure is applied to the working fluid. More specifically, the concentricity of the inner and outer peripheral surfaces of the resin layer 5 in a cross section perpendicular to the tube longitudinal direction, i.e., a distance between a center of the inner peripheral surface of the inner resin layer 2 and a center of the outer peripheral surface of the outer resin layer 4 is preferably 0.08 mm or less.

Furthermore, in order to increase the pressure resistance of the braided tube 1, the thickness of the braided tube 1 (the entire thickness of the inner resin layer 2, the braided wire 3, and the outer resin layer 4) is desired to be as homogeneous as possible. Specifically, a value obtained by subtracting the minimum value of the wall thickness of the braided tube 1 from the maximum value of the wall thickness of the braided tube 1 is preferably not more than 0.16 mm.

(Connector 15 and a Connection Structure Between the Connector 15 and the Braided Tube 1)

Figure 4A:
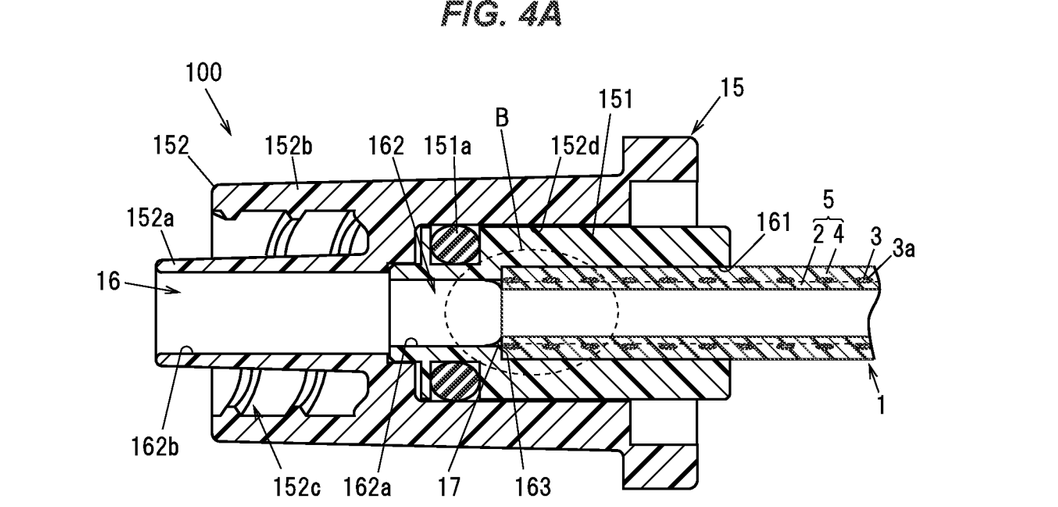
FIG. 4A is a cross-sectional view of a connecting portion between a connector and the braided tube.
Figure 4B:
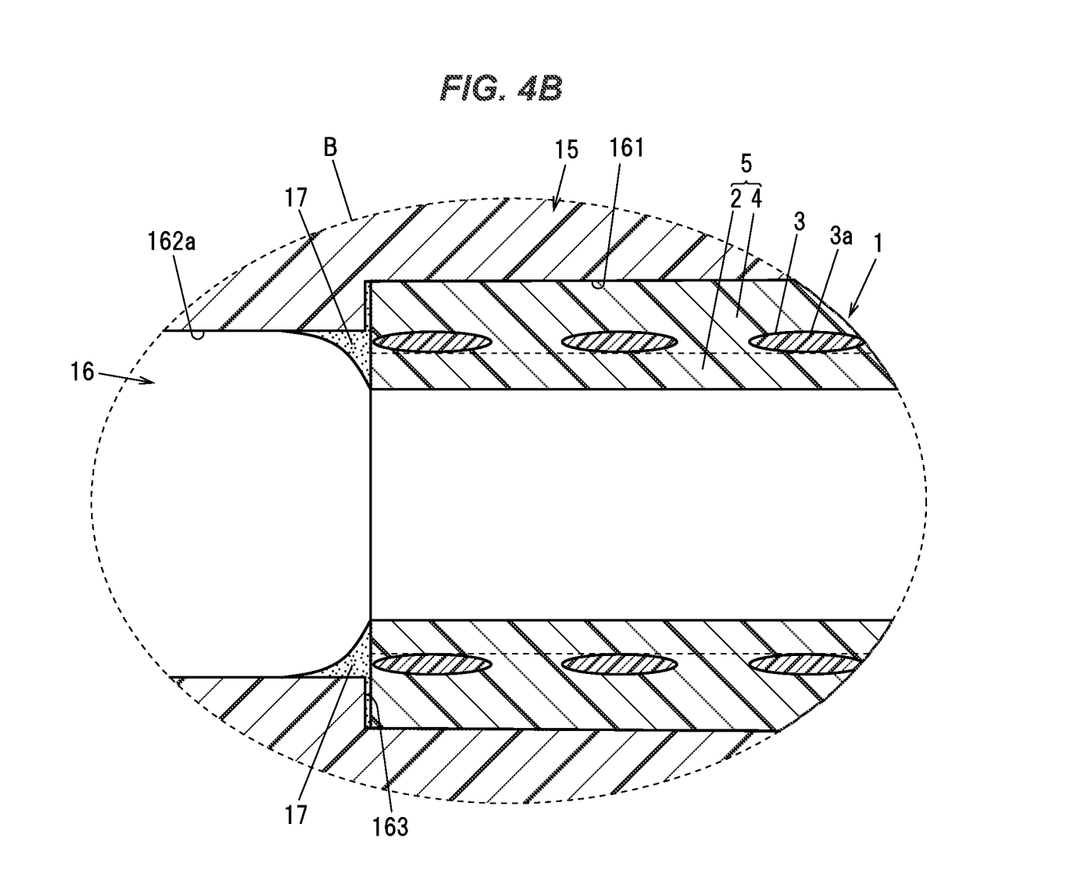
FIG. 4B is an enlarged view of a part B of the connecting portion between the connector and the braided tube in FIG. 4A.

FIG. 4A is a cross-sectional view of a connecting portion between the connector 15 and the braided tube 1. FIG. 4B is an enlarged view of a part B of the connecting portion between the connector 15 and the braided tube 1 in FIG. 4A.

As shown in FIGS. 4A and 4B, the connector 15 includes a tube housing section 161 for accommodating the one end of the braided tube 1, and the braided tube 1 accommodated in the tube housing section 161 and the connector 15 are adhesively fixed by an adhesive 17.

In more detail, the connector 15 includes a flow path 16 for passing the working fluid flowing through the braided tube 1, and the tube housing section 161 for accommodating the one end of the braided tube 1 is formed at one end of the flow path 16. Hereinafter, the flow path 16 other than the tube housing section 161 will be referred to as a liquid flow passage 162.

The liquid flow passage 162 is communicated with the tube housing section 161, and an end portion of the liquid flow passage 162 (a first liquid flow passage 162a to be described later) on the side of the tube housing section 161 is configured to have an inner diameter which is smaller than an inner diameter of the tube housing section 161 and larger than the inner diameter of the braided tube 1. In the present embodiment, the inner diameter of the liquid flow passage 162 at an end on the side of the tube housing section 161 (to be described later as a first liquid flow passage 162a) is configured to be larger than the inner diameter of the braided wire 3 in the braided tube 1 (or the outer diameter of the inner resin layer 2). A step portion (level difference) 163 for suppressing excessive insertion of the braided tube 1 is formed between the inner peripheral surface of the tube housing section 161 and the inner peripheral surface of the liquid flow passage 162.

In the present embodiment, a connector 15 has a two-part (split) structure, and includes a base portion 151 including the tube housing section 161 and the first liquid flow passage 162a as a part of the liquid flow passage 162, and a connecting portion 152 configured to be connected to a receiving side connector (not shown) and including a second liquid flow passage 162b as the other part of the liquid flow passage 162. A tip portion of the connecting portion 152 is provided with a cylindrical inner tube 152a for covering the second liquid flow passage 162a and an outer tube 152b which is provided coaxially with and the inner tube 152a and separated from the inner tube 152a in a radial direction. At the inner peripheral surface of the tube 152b, a female threaded portion 152c with a spiral ridge is provided, and the female threaded portion 152c is configured to screwed with a male threaded portion at an end of the receiving side connector in such a manner that the connector 15 is connected to the receiving side connector. The connecting portion 152 includes a base housing portion 152d for housing a tip portion of the base portion 151, and the base portion 151 and the connecting portion 152 are fixed to each other in a state that the tip portion of the base portion 151 is inserted into the base housing section 152d. At an outer peripheral surface of the tip portion of the base portion 151, an O-ring 151a is provided, and the O-ring 151a is configured to seal a space between the outer peripheral surface of the base portion 151 and the inner peripheral surface of the base housing section 152d. The specific structure of the connector 15 is not limited thereto, and may be, e.g., not a two-part configuration.

After the zealous study, the present inventors found that, when the working fluid is pressurized, the pressure resistance cannot be obtained sufficiently at the connecting portion between the connector 15 and the braided tube 1 so that the leakage may occur. As a result of the further study, the present inventors found that, when the working fluid is pressurized, the working fluid may enter into the void 6 between the braided wire 3 and the resin layer 5, and the working fluid entered into the void 6 may cause the deformation or breakage of the braided tube 1. The present inventors found that the aforementioned problem becomes remarkable particularly in the case where the step portion 163 is small so that the braided wire 3 is exposed even though an end face of the braided tube 1 is brought into contact with the step portion 163 (i.e. the inner diameter of the first liquid flow passage 162a is larger than the inner diameter of the braided wire 3), or, in the case where the end face of the braided tube 1 is largely separated from the step portion 163.

Therefore, in the medical braided tube assembly 100 according to the present embodiment, in order to suppress the entrance of the working fluid into the void 6 between the braided wire 3 and the resin layer 5, an adhesive 17 is provided so as to seal an entire periphery of the braided wire 3 at the end face of the braided tube 1. Thus, the pressure resistance at the connecting portion between the connector 15 and the braided tube 1 is improved, so that it is possible to suppress the deformation or breakage of the braided tube 1 when the working fluid is pressurized.

The adhesive 17 is preferably provided over the inner resin layer 2, the braided wire 3, and the outer resin layer 4 on the end face of the braided tube 1. Moreover, the adhesive 17 provides a function of adhesively fixing the braided tube 1 to the connector 15, and a function of sealing a space between the outer peripheral surface of the braided tube 1 and the connector 15. Therefore, it is preferable that the adhesive 17 is provided over the inner peripheral surface of the flow path 16 and the end face of the braided tube 1 without a gap.

If the void 6 is large, the possibility that the working fluid will enter the void 6 increases. Therefore, as described above, the width w of the void 6 in the cross section perpendicular to the tube longitudinal direction is 30 µm or less, more preferably 25 µm or less. Namely, by setting the width w of the void 6 to be 30 µm or less, it is possible to improve not only the transparency of the braided tube 1 but also the pressure resistance at the connecting portion between the connector 15 and the braided tube 1.

In the present embodiment, the inner peripheral surface of the tube housing section 161 of the connector 15 is formed in a tapered shape in which the inner diameter gradually decreases from the insertion side of the braided tube 1 to a side of the liquid flow passage 162. Further, the tube housing section 161 is designed in such a manner that the inner diameter on the side of the liquid flow passage 162 is smaller than the outer diameter of the braided tube 1, and the inner diameter at an end portion on the insertion side is larger than the outer diameter of the braided tube 1.

The inner diameter of an end portion on the side for inserting the braided tube 1 in the tube housing section 161 is designed to be larger than the outer diameter of the braided tube 1, so that the braided tube 1 can be easily inserted into the tube housing section 161. Furthermore, the inner diameter of an end portion on the liquid flow passage 162 in the tube housing section 161 is designed to be smaller than the outer diameter of the braided tube 1. When the braided tube 1 is pushed, the braided tube 1 is pushed into the tube housing section 161 while being deformed to be reduced in diameter, so that the outer peripheral surface of the braided tube 1 and the inner peripheral surface of the tube housing section 161 are firmly adhered to each other, and the pressure resistance is improved. Furthermore, the tube housing section 161 is designed to be tapered in such a manner that the tube housing section 161 is applicable to a slight variation of the outer diameter of the braided tube 1, thereby improving the versatility of the connector 15.

In the present embodiment, the braided tube 1 is pushed deeply inside the tube housing section 161 (until the vicinity of the step portion 163) while being deformed to be reduced in diameter, the adhesive 17 is provided in a fillet shape over the inner peripheral surface of the liquid flow passage 162 and the end face of the braided tube 1. The end face of the braided tube 1 and the step portion 163 may be in contact with each other, and may not be in contact with each other.

In the present embodiment, the adhesive 17 is made of an ultraviolet curable resin that is cured by irradiation with ultraviolet rays. The connector 15 is made of a material that transmits ultraviolet rays so that the adhesive 17 can be irradiated with ultraviolet rays. The connector 15 is preferably made of a material that transmits visible light, and like the braided tube 1, the connector 15 is more preferably made of a material having a high transparency in such a manner that the outer shape of the transparent liquid flowing through the flow path 16 and the bubbles contained in the liquid can be visually recognized. In the present embodiment, the connector made of polycarbonate is used.

When the connector 15 is attached to the end portion of the braided tube 1, the adhesive 17 is firstly applied on the end portion of the braided tube 1. At this time, a predetermined amount of the adhesive 17 is applied to the end face of the braided tube 1 and the outer peripheral surface of the end portion of the braided tube 1. The adhesive 17 is applied to seal the entire periphery of the braided wire 3 at the end face of the braided tube 1 (to cover a portion of the braided wire 3). Then, the end portion of the braided tube 1 coated with the adhesive 17 is inserted into the tube housing section 161 of the connector 15. At this time, the braided tube 1 is pushed to the vicinity of the step portion 163 while being reduced in diameter, the adhesive 17 applied to the end face of the braided tube 1 spreads therearound so that the adhesive 17 is provided in the form of a fillet over the inner peripheral surface of the liquid flow passage 162 and the end face of the braided tube 1. Further, the adhesive 17 is filled in a slight gap between the outer peripheral surface of the braided tube 1 and the inner peripheral surface of the tube housing section 161. In this state, when the connector 15 is irradiated with ultraviolet light from the light source, the ultraviolet light passes through the connector 15 to reach the adhesive 17, and the adhesive 17 is cured. Thus, the medical braided tube assembly 100 is obtained.

Operation and Effect of the Embodiment

As described above, the medical braided tube assembly 100 according to the present embodiment is configured in such a manner that the braided tube 1 accommodated in the tube housing section 161 the connector 15 are adhesively fixed by the adhesive 17, and the adhesive 17 is provided to seal the entire periphery of the braided wire 3 at the end face of the braided tube 1.

With this configuration, it is possible to suppress the entrance of the working fluid into the void 6 between the braided wire 3 and the resin layer 5, so that it is possible to suppress the deformation or breakage of the braided tube 1 when the working fluid is pressurized, thereby improving the pressure resistance at the connecting portion between the connector 15 and the braided tube 1.

Summary of the Embodiment

Next, the technical ideas grasped from the above-described embodiments will be described with the aid of the reference characters and the like in the embodiments. It should be noted, however, that each of the reference characters and the like in the following descriptions is not to be construed as limiting the elements in the appended claims to the members and the like specifically shown in the embodiments.

[1] A medical braided tube assembly (100) comprising: a braided tube (1) comprising a hollow cylindrical inner resin layer (2), a braided wire (3) including braided strands (3a) and being provided over a periphery of the inner resin layer (2), and an outer resin layer (4) provided to cover peripheries of the inner resin layer (2) and the braided wire (3); and a connector (15) provided at an end portion of the braided tube (1), wherein the connector (15) includes a tube housing section (161) for accommodating the end portion of the braided tube (1), wherein the braided tube (1) accommodated in the tube housing section (161) and the connector (15) are adhesively fixed by an adhesive (17), wherein the adhesive (17) is provided to seal an entire periphery of the braided wire (3) at an end face of the braided tube (1).

[3] The medical braided tube assembly (100) according to [1] or [2], wherein the connector (15) further comprises a flow path (16) for passing a working fluid flowing through the braided tube (1), wherein the tube housing section (161) for accommodating the end portion of the braided tube (1) is provided at an end portion of the flow path (16), wherein the adhesive (17) is provided over an inner peripheral surface of the flow path (16) and the end face of the braided tube (1).

[4] The medical braided tube assembly (100) according to [3], wherein the flow path (16) includes the tube housing section (161) and a liquid flow passage (162) which is communicated with the tube housing section (161), wherein an end portion of the liquid flow passage (162) on a side of the tube housing section (161) has an inner diameter which is smaller than an inner diameter of the tube housing section (161) and larger than an inner diameter of the braided tube (1), wherein a step portion (163) for suppressing excessive insertion of the braided tube (1) is provided between an inner peripheral surface of the tube housing section (161) and an inner peripheral surface of the liquid flow passage (162), wherein the adhesive (17) is provided over the inner peripheral surface of the liquid flow passage (162) and the end face of the braided tube (1).

[5] The medical braided tube assembly (100) according to [4], wherein the inner peripheral surface of the tube housing section (161) has a tapered shape in which the inner diameter gradually decreases from an insertion side of the braided tube (1) to a side of the liquid flow passage (162), wherein the inner diameter of the tube housing section (161) on the side of the liquid flow passage (162) is smaller than an outer diameter of the braided tube (1).

[6] The medical braided tube assembly (100) according to any one of [1] to [5], wherein the adhesive (17) comprises an ultraviolet curable resin that is cured by irradiation with ultraviolet rays, and the connector (15) comprises a material that transmits ultraviolet rays.

[7] The medical braided tube assembly (100) according to any one of [1] to [6], wherein a width of a void (6) formed around the strand (3*a*) of the braided wire (3) in a cross section perpendicular to a tube longitudinal direction is 30 µm or less.

Although the embodiments of the present invention have been described above, the embodiments described above do not limit the invention according to the claims. Further, it should be noted that not all of the combinations of features described in the embodiments are essential to the means for solving the problems of the invention.

The present invention can be appropriately modified and implemented without departing from the spirit of the present invention. For example, in the above embodiment, the medical braided tube assembly 100 to be used for the indeflator 10 is described, the application use of the medical braided tube assembly 100 is not limited thereto.

Although the invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:

1. A medical braided tube assembly comprising:
    a braided tube comprising a hollow cylindrical inner resin layer, a braided wire including braided strands and being provided over a periphery of the inner resin layer, and an outer resin layer provided to cover the periphery of the inner resin layer and a periphery of the braided wire; and
    a connector provided at an end portion of the braided tube,
    wherein the connector includes a tube housing section for accommodating the end portion of the braided tube,
    wherein the braided tube accommodated in the tube housing section is adhesively fixed by an adhesive,
    wherein the adhesive is provided to seal an entire periphery of the braided wire at an end face of the braided tube,
    wherein the inner resin layer is an innermost layer of the braided tube,
    wherein the connector further comprises a flow path that is configured to come into direct contact with a working fluid when a working fluid is flowing through the braided tube, and
    wherein the adhesive constitutes part of the flow path.

2. The medical braided tube assembly according to claim 1, wherein the adhesive is provided over the inner resin layer, the braided wire, and the outer resin layer at the end face of the braided tube.

3. The medical braided tube assembly according to claim 1,
    wherein the tube housing section for accommodating the end portion of the braided tube is provided at an end portion of the flow path,
    wherein the adhesive is provided over the end face of the braided tube.

4. The medical braided tube assembly according to claim 3,
    wherein the flow path includes the tube housing section and a liquid flow passage which is communicated with the tube housing section,
    wherein an end portion of the liquid flow passage on a side of the tube housing section has an inner diameter which is smaller than an inner diameter of the tube housing section and larger than an inner diameter of the braided tube,
    wherein a step portion for suppressing excessive insertion of the braided tube is provided between an inner peripheral surface of the tube housing section and an inner peripheral surface of the liquid flow passage,
    wherein the adhesive is provided over the inner peripheral surface of the liquid flow passage and the end face of the braided tube.

5. The medical braided tube assembly according to claim 4,
    wherein the inner peripheral surface of the tube housing section has a tapered shape in which an inner diameter gradually decreases from an insertion side of the braided tube to a side of the liquid flow passage,
    wherein the inner diameter of the tube housing section on the side of the liquid flow passage is smaller than an outer diameter of the braided tube.

6. The medical braided tube assembly according to claim 1, wherein the adhesive comprises an ultraviolet curable resin that is cured by irradiation with ultraviolet rays, and the connector comprises a material that transmits ultraviolet rays.

7. The medical braided tube assembly according to claim 1, wherein each of the strands of the braided wire are located in a respective void, each void having a width in a cross section perpendicular to a tube longitudinal direction that is 30 µm or less.

8. The medical braided tube assembly according to claim 1, wherein the inner resin layer, the braided wire, and the outer resin layer constitute the end face of the braided tube.

9. The medical braided tube assembly according to claim 1, wherein the inner resin layer is configured to come into direct contact with the working fluid when the working fluid is flowing through the braided tube.

10. The medical braided tube assembly according to claim 1, wherein the connector includes a base portion that houses the end portion of the braided tube, and a connecting portion detachably connectible to the base portion.

11. The medical braided tube assembly according to claim 10, wherein the connecting portion is connectible to another connector.

12. A medical braided tube assembly comprising:
    a braided tube comprising a hollow cylindrical inner resin layer, a braided wire including braided strands and being provided over a periphery of the inner resin layer, and an outer resin layer provided to cover the periphery of the inner resin layer and a periphery of the braided wire; and
    a connector provided at an end portion of the braided tube,
    wherein the connector includes a tube housing section for accommodating the end portion of the braided tube,
    wherein the braided tube accommodated in the tube housing section is adhesively fixed by an adhesive,
    wherein the adhesive is provided to seal an entire periphery of the braided wire at an end face of the braided tube,
    wherein the inner resin layer is an innermost layer of the braided tube, and
    wherein the connector further comprises a flow path for passing a working fluid when a working fluid is flowing through the braided tube, and both the connector and the adhesive are configured to come into direct contact with the working fluid when the working fluid is flowing through the braided tube.

13. A medical braided tube assembly comprising:
a braided tube comprising a hollow cylindrical inner resin layer, a braided wire including braided strands and being provided over a periphery of the inner resin layer, and an outer resin layer provided to cover a periphery of the inner resin layer and a periphery of the braided wire; and
a connector provided at an end portion of the braided tube,
wherein the connector includes a tube housing section for accommodating the end portion of the braided tube,
wherein the braided tube accommodated in the tube housing section is adhesively fixed by an adhesive,
wherein the adhesive is provided to seal an entire periphery of the braided wire at an end face of the braided tube,
wherein the inner resin layer is an innermost layer of the braided tube, and
wherein the adhesive contacts only the end face of the braided tube and an inner surface of the connector that defines a liquid flow passage.

* * * * *